United States Patent [19]

Zanakis

[11] Patent Number: 5,630,422
[45] Date of Patent: May 20, 1997

[54] DIAGNOSTIC SYSTEM FOR DETECTING AND INDICATING CRANIAL MOVEMENTS

[76] Inventor: Michael F. Zanakis, 1 Ken Pl., Port Jefferson Station, N.Y. 11776

[21] Appl. No.: 524,989

[22] Filed: Sep. 8, 1995

[51] Int. Cl.$^6$ ..................................................... A61B 5/11
[52] U.S. Cl. ......................... 128/664; 128/653.1; 128/782
[58] Field of Search .................................. 128/664, 653.1, 128/774, 782; 378/205, 206; 356/247

[56] References Cited

U.S. PATENT DOCUMENTS

| | | |
|---|---|---|
| 4,813,436 | 3/1989 | Au . |
| 5,249,581 | 10/1993 | Horbal et al. . |
| 5,394,457 | 2/1995 | Leibinger et al. . |
| 5,446,548 | 8/1995 | Gerig et al. . |
| 5,458,123 | 10/1995 | Unger . |
| 5,462,065 | 10/1995 | Cusimano . |

*Primary Examiner*—Marvin M. Lateef
*Assistant Examiner*—Shawna J. Shaw
*Attorney, Agent, or Firm*—Michael Ebert

[57] ABSTRACT

A diagnostic system for detecting and indicating cranial movements in a human subject whose brain case is composed of a plurality of articulated bones which define the cranium. The system includes infrared reflector elements placed on selected bones of the cranium and infrared video cameras directed at the cranium emitting infrared light during a test period that is reflected by the elements and picked up to produce in an image analyzer associated with the cameras a two or three-dimensional image providing information regarding relative motion between the reflector elements. This information is supplied to a computer programmed to reconstruct the perceived motion as a diagram illustrating cranial movements during the test period. To eliminate the effect of motion from other kinetically active parts of the body, such as muscle movement variables, respiration and heart beat, included in the system is an EMG unit associated with separate electrode elements placed on the head and torso of the subject to measure and indicate muscle activity. Also electrodes are placed on the torso to monitor the EKG of the subject. The EMG and EKG indications are subtracted from the reading so that the motion detected of cranial bone movement is indicative only of this movement.

9 Claims, 3 Drawing Sheets

DIAGNOSTIC SYSTEM FOR DETECTING AND INDICATING CRANIAL MOVEMENTS

BACKGROUND OF INVENTION

1. Field of Invention

This invention relates to a diagnostic system adapted to measure accurately minute cranial movements in a human subject and to determine whether these movements deviate from a normal cranial movement pattern and thereby facilitate treatment of the patient by cranial manipulation.

2. Status of Prior Art

In a human skull, the eight cranial bones which together form a hollow protective brain case or cranium are the occipital, sphenoid, ethmoid and frontal bones, as well as the paired temporal and parietal bones. Skull articulations are generally serrated sutures. The concern of the present invention is with the movements of articulated cranial bones and the degree to which deviations from a normal pattern of rhythmic movement reflect a pathological condition that lends itself to treatment by osteopathic manipulative therapy.

In this background section, reference will be made to published papers in scientific journals listed at the end of the section, each paper being identified by a number (1 to 22).

The basic principles underlying the practice of osteopathy center around the need to establish the optimal structure and function of the body in order to prevent or alleviate illness. Historically, allopathy seeks to treat illness by eradicating foreign offenders, and this method of treatment often results in merely alleviating the symptoms. The osteopathic approach which deals with how disturbances in the musculoskeletal system affect other bodily parts, is to consider the body's defenses in attempting to overcome illness. Osteopathic treatment is aimed at improving the body's structural components, thereby improving the body's functional capabilities and allowing the body to heal itself.

Until recently, the efficacy of osteopathic treatment was determined largely by subjective analysis of clinical improvement and patient testimony. During the past two decades, various modalities have been employed in order to objectively demonstrate the efficacy of osteopathic manipulative therapy (OMT). Toward this end, instrumentation such as pressure transducers, forced-displacement meters, and electromyography (EMG) have been utilized (See refs. 9, 10, 13, 16, 18 and 20).

The aim of the present invention is to objectively measure, confirm and evaluate cranial mobility by focusing on the movement of the cranial bones, and to correlate subjective perception of cranial movement with kinematically acquired actual movement. Confirmation can be achieved by isolating the cranial bone movement from movements arising from other parts of the body. The objective measurement of cranial mobility is useful in diagnosis in determining cranial bone alterations as a result of pathological conditions. Also, the results of cranio-facial manipulation can be quantified using a system in accordance with the invention.

Craniosacral theory in osteopathy is based on essentially four factors: namely, (a) movement of bone structures, (b) movement of membranous structures, (c) motility of the central nervous system, and (d) movement of fluids, such as cerebrospinal fluid (CSF) (See refs. 5, 9 and 10 for complete review). This theory postulates that a cranial rhythmic impulse exists which is palpable at various locations in the body, with an average rate of 8 to 14 cycles per minute. This impulse does not correspond with other well defined pulses such as respiration and heart beat. The cranial rhythmic impulse can be evaluated with respect to rate, amplitude and quality, with quality defined in terms of the characteristic wave form (See ref. 10).

The concepts underlying cranial theory which tie it in with other forms of osteopathy involve the body as a unity and its ability for autoregulation which maintains homeostasis. It also takes into account the crucial interrelationship between body structure and function. This theory was originally developed from a study of the structure of the cranial sutures. It was postulated that the orientation of the sutures were such that movement about the suture lines was possible (See refs. 9, 10 and 16). Originally it had been believed that movement of the cranial bones was possible in an infant or child, but not in adulthood, for then these sutures had ossified to the point were movement was no longer possible (See refs. 1 and 17).

However, recent studies have demonstrated the relationship between variations in the volume of cerebrospinal fluid (CFC) and changes in intracranial pressure (See refs. 2, 6, 8, 11, 12, 14 and 22). Marmarou, et al. (see ref. 12) demonstrated that many inanimate containers have ideal elastic properties. Such properties include a coefficient of compliance which does not vary with time or is constant for all degrees of expansion of the container. In such an ideal container, pressure varies linearly with volume and the slope of the volume-pressure curve (or compliance) is constant. Pressure and volume in the compartments containing CSF are not linearly related (See ref. 12). These findings led Marmarou, et al. to conclude that various structures within the central nervous system (CNS) alter their structure or function in order to accommodate various challenges to the system. Marmarou, et al. attributed this ability to the brain, ventricles and blood vessels.

Two of the major assumptions upon which Marmarou, et al. and others (See refs. 2, 8, 14 and 22) have based their findings are that the cranium is a fixed structure, unable to alter its shape or capacity to accommodate any changes in the system. Furthermore, the dura mater, likewise, is a firm fibrous structure which similarly cannot adapt to changes in the structures enveloped within it. Studies performed have demonstrated that the administration of a bolus of fluid into the ventricular system causes a temporary increase in pressure which then returns to steady state (See refs. 11 and 12). It is the conclusion of these investigators that the increased volume causes a chain of events in the circulartory/ventricular system of CNS to modify its function and enable the body to overcome the insult and reestablish homeostasis (See refs. 11 and 12).

One group of investigators (See ref. 11) concluded that the individual effects of these processes relating to pressure are difficult to isolate by experimental means, since formation, absorption and elasticity are mutually interactive, and their combined effects upon intracranial pressure are hydrodynamically complex. One study, performed on infants with hydrocephalus, concluded that a much larger amount of fluid is necessary to produce hydrocephalus than in adults due to the opened suture lines at the fontenelles (See ref. 17).

It was further concluded that the mobility of the cranial bones was able to compensate for increase in CSF volume until the volume was such that the system was overwhelmed (See ref. 17). Intracranial monitoring studies have demonstrated that changes in the cerebrospinal fluid pulse waves exist under conditions of hypercapnia and increased intracranial pressure (See ref. 14). Several investigators have recognized that the cerebrospinal fluid pulse wave was similar to the arterial pulse, but the exact origin of the wave has not been determined (See ref. 14). One investigator (see ref. 3) believed that the wave emanates from the choroid plexus. However, another group (See ref. 4) demonstrated that the cerebrospinal fluid pulse wave could be observed in the lumbar spinal canal when the cervical fluid pathway had been obstructed. A more recent study concluded that the cerebrospinal fluid pulse wave is derived from the transmission of an arterial pulse into the cerebral veins, and that the pulsations within the thin-walled veins are transmitted to the CSF (See ref. 14).

A striking feature of these studies is that many of the conclusions are based on the assumption that the structure and function of the cranium and dura mater are limited and constant. If, however, these assumptions were proven to be false, conclusions drawn from them would likewise be in error and an alternative method of compensation by the CNS would be possible.

There have been studies performed which seek to objectively demonstrate the phenomenon of Cranial Rhythmic Impulse. This is the phenomenon which osteopathic physicians trained in cranial therapy are able to palpate. These studies have been approached anatomically (histologically) and physiologically.

Anatomical or histological studies have focused largely on the suture lines. Retzlaff, et al. (See ref. 15) found the existence, within the suture line, fibrous connective tissue, elastic connective tissue, blood vessels, nerves and sensory endings. They further hypothesized that pain may result from compression along these suture lines due to the structures contained within the suture. Further analysis of the cranial bones and suture lines led Retzlaff, et al. to define four articular patterns observed between parietal bones and adjacent cranial bones: (a) plane suture, (b) squamous suture, (c) serrate suture, and (d) denticulate suture. Retzlaff, et al. further suggested that the plane and squamous sutures allow for a sliding and separating movement, while the serrate and denticulate articulations permit a hinge type of movement. The general conclusion of these investigations is that movement of the cranial bones along suture lines is highly probable.

Physiological studies include a series of experiments performed by Frymann (See ref. 7) designed to investigate the motion of the living cranium. Frymann observed a rhythm which was synchronous with respiration and cardiac activity, and another slower wave motion independent of the other two. Other investigators performed experiments on anesthetized squirrel monkeys to measure parietal bone movement (See ref. 16). They found that when the monkey's head was allowed free movement in a stereotaxic apparatus, the pattern of movement was directly related to cardiac and respiratory activity. With limited movement in the stereotaxic apparatus, right parietal bone movement corresponded to respiratory activity, whereas the left parietal bone appeared to move independently. Complete immobilization resulted in independent motions of each parietal bone with resulting independent wave motion. It was further noted that flexion and extension of the monkey's body resulted in an increased amplitude of these waves. It was concluded from this study that this direct correlation of vertebral column movement and parietal bone movement indicates that alterations in cerebrospinal fluid are responsible for bone movement.

Another study correlated mechano-electric patterns acquired using electrodes on various portions of the subject's body with subjective findings of a physician during craniosacral diagnosis and treatment. This study found that a strong correlation existed between the physician's subjective findings and the data acquired from the sensors (See ref. 20).

A more recent study aimed at identifying parietal bone mobility in anesthetized cats demonstrated that rotational and lateral movement of the parietal bones occur in reference to the medial sagittal suture (See ref. 1). In this study, an isotonic monitoring device was attached to the exposed cranium of anesthetized cats. Data was collected during spontaneous movement as well as movement under stress (i.e., increased intracranial pressure) when a compressive force was applied, a bolus of artificial CSF injected, or induction of hypercapnia.

Their results indicated that cranial motion was affected by insults or challenges to the system. Furthermore, restriction of head movement (i.e., by placement in a stereotaxic apparatus) resulted in a decrease in cranial motion as well as a decrease in the amount of compensation by cranial motion to an imposed challenge. These investigators concluded that lateral and rotational mobility of the parietal bones at the sagittal suture contribute to cranial compliance. They further hypothesize that cranial sutures play an important role in cranial compliance, and have the ability to absorb energy.

Various other studies have demonstrated craniosacral pathology in children with diagnosed emotional or behavioral disorders or learning disabilities (See ref. 21). This investigator has also found a positive correlation between complicated obstetrical delivery and restricted craniosacral motion. These studies, in conjunction with documentation of successful therapy of illnesses and disorders such as dyslexia, reactive and endogenous depressions and hyperkinesis (see ref. 9) lend strong support to the craniosacral theory and practice.

Although utilized in various other aspects (e.g., gait analysis), motion analysis using kinematics has not heretofore been considered useful in testing the hypothesis of cranial movement. No studies have heretofore been performed which allow a two or three-dimensional reconstruction of cranial movement in a human subject. This has been due to the technology itself, for the available kinematic systems lacked the sensitivity to detect minute movements at a reasonable working distance.

REFERENCES

1. Adams T., Heisey R. S., Smith M. C., Briner B. J. Parietal Bone Mobility in the Anesthetized Cat. JAOA 92(5):599–622, 1992.
2. Adams T., Heisey S. R., Smith M. C., Steinmetz M. A., Hartman J. C., Fry H. K. Thermodynamic Technique for the Quantification of Regional Blood Flow. Am. J. Physiol 238:H682–H696, 1980.
3. Bering E. A. Choroid Plexus and Arterial Pulsation of Cerebrospinal Fluid. Arch. Neurol. Psychiatry 73:165–172, 1955.
4. Dunbar H. S., Gunthrie T. C., Karpell B. A Study of the Cerebrospinal Fluid Pulse Wave. Arch. Neurol 14:624–630, 1966.
5. Ettlinger H., Gintis B. Craniosacral Concepts in An Osteopathic Approach to Diagnosis and Treatment. E. L. DiGiovanna and S. Schiowitz eds. p. 369–401. J. B. Lippincott Co, New York, 1991.
6. Fisher M. J., Heisey S. R., Adams T., Traxinger D. L. Cerebrospinal Fluid Transients Induced by Hipercapnia. Am. J. Physiol 245:R701–R705, 1983.

7. Fryman V. M. A Study of the Rhythmic Motions of the Living Cranium. JAOA 70:928–945, 1971.
8. Heisey S. R, Adams T., Fisher M. J., Dang W. Effect of Hypercapnia and Cerebral Perfusion Pressure on Cerebrospinal Fluid Production in Cat. Am. J. Physiol. 244: R224–R227, 1983.
9. Inabinet C. The Cranial Connection: A Professional's Introduction to Cranial Osteopathy. Phoenix, Ariz. 1986.
10. Kappler R. E. Osteopathy in the Craniel Field. OP/The Osteopathic Physician. 13–18, 1979.
11. Marmarou A., Shulman K., Rosende R. M. A Nonlinear Analysis of the Cerebrospinal Fluid System and Intracranial Pressure Dynamics. J. Neurosurg. 48:332–344, 1978.
12. Marmarou A., Shulman K., LaMorgese J. Compartmental Analysis of Compliance and Outflow Resistance of the Cerebrospinal Fluid System. J. Neurosurg. 43:523–534, 1975.
13. Norton J. M. A Tissue Pressure Model for Palpatory Perception of the Cranial Rhythmic Impulse. JAOA 91(10):975–994, 1991.
14. Portnoy H. D., Chopp M., Branch C., Shannon M. B. Cerebrospinal Fluid Pulse Waveform as an Indicator of Cerebral Autoregulation. J. Neurosurg. 56:666–678, 1982.
15. Retzlaff E. W. Structural and Functional Concepts of Craniosacral Mechanisms in P. E. Greenman ed. Concepts and Mechanisms of Neuromuscular Functions p. 58–65, Springer: New York, 1984.
16. Retzlaff E. W., Michael D. K., Roppel, R. M. Cranial Bone Mobility. JAOA 75:869–873, 1975.
17. Shapiro K., Fried A., Marmarou A. Biomechianical and Hydrodynamic Characterization of the Hydrocephalic Infant. J. Neurosurg. 63:69–75, 1985.
18. Sprovieri, J. Biomechanical Engineering Shows Effectiveness of OMT. THE DO 32(4):72–73,1991.
19. Upledger J. E., Vredevoogd J. D. Craniosacral Therapy, Eastland Press: Chicago, 1983.
20. Upledger, J. E. Mechano-electric Patterns During Craniosacral Osteopathic Diagnosis and Treatment. JAOA 78:782–791, 1979.
21. Upledger, J. E. The Relationship of Craniosacral Examination Findings in Grade School Children with Developmental Problems. JAOA 77:738–754, 1978.
22. Wilkinson H. A., Schuman N., Rugiero J. Nonvolumetric Methods of Detecting Impaired Intracranial Compliance or Reactivity. J. Neurosurg. 50:758–767, 1979.

SUMMARY OF INVENTION

The main object of this invention is to provide a diagnostic system for detecting and indicating cranial movements in a human subject whose brain case is composed of a plurality of articulated bones which define the cranium, the system eliminating the effects of motion from other kinetically active parts of the body.

More specifically, an object of the invention is to provide a system of the above type which makes use of infrared video cameras in conjunction with infrared reflector elements placed on selected bones of the cranium to detect bone motions in two or three dimensions.

Also an object of the invention is to provide a system which facilitates the practice of cranial osteopathy and is also useable for diagnostic and screening purposes to quantify cranial mobility and the use of craniosacral therapy in treating various disorders.

Briefly stated, the objects are attained by a diagnostic system for detecting and indicating cranial movements in a human subject whose brain case is composed of a plurality of articulated bones which define the cranium. The system includes infrared reflector elements placed on selected bones of the cranium and infrared video cameras directed at the cranium emitting infrared light during a test period that is reflected by the elements and picked up to produce in an image analyzer associated with the cameras an image providing information regarding relative motion between the reflector elements. This information is supplied to a computer programmed to reconstruct the motion as a diagram illustrating cranial movement during the test period.

To eliminate the effect of motion from other kinetically active parts of the body, such as muscular movement variables, respiration and heart beat, included in the system is an EMG unit associated with separate electrode elements placed on the head and torso of the subject to measure and indicate muscle activity. Also electrodes are placed on the torso to monitor the EKG of the subject. The EMG and EKG indications are subtracted from the reading so that the motion detected of cranial bone movement is indicative only of this movement.

BRIEF DESCRIPTION OF DRAWINGS

For a better understanding of the invention, as well as other objects thereof, reference is made to the following detailed description of the invention to be read in conjunction with the accompanying drawings in which.

DESCRIPTION OF INVENTION

Figure 1:
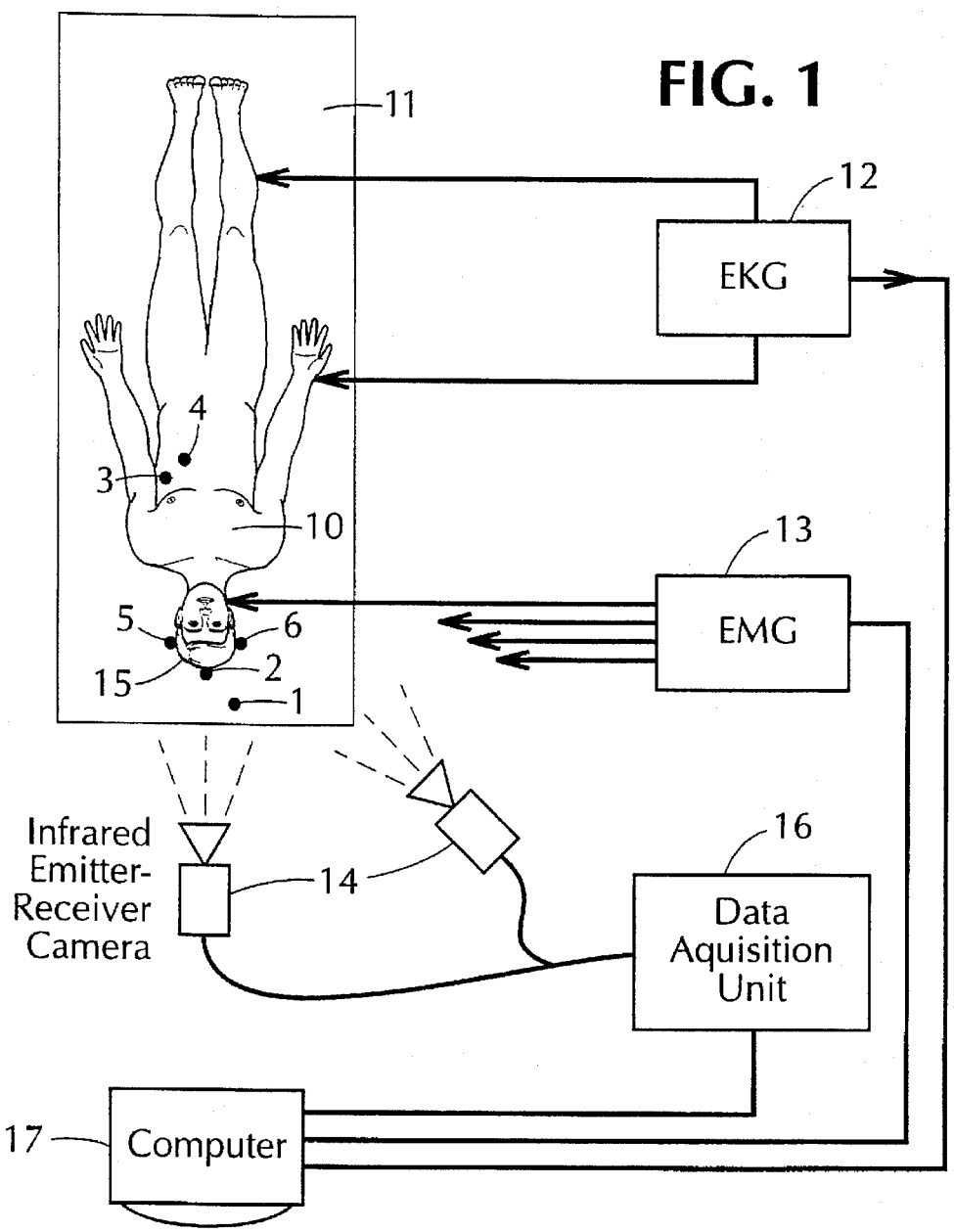
FIG. 1 illustrates a system in accordance with the invention as applied to a subject lying on a table.

As shown in FIG. 1, to test a given patient or subject 10, the subject is asked to remove all upper body clothing and wear a loose fitting gown that opens in the front only enough to palpate the sternum and fifth left intercostal space. Subject 10 is asked to lie down on an examination table 11 in the supine position.

Two points are chosen on each of the temporal, parietal and frontal bones. The points are sponged with alcohol to disinfect the scalp. The area is then cleaned, and sterile water soluble lubricating jelly ("K-Y") is applied to the area to mat down the hair. A 1 inch #3 acupuncture needle (sterile and disposable) is inserted through the scalp and into each point of each bone. By firmly inserting the needle into the bone, it becomes well anchored. Quarter inch diameter hemispherical infrared reflectors are attached to the needle shafts. Other reflectors are placed directly on the body and kept in place with two-face tape applied to the reflector base and adhered to the skin.

In preliminary experiments, anchoring the reflectors directly to the parietal bone was needed to detect movement of the bony structures. Therefore, if the bone moved, the reflectors would move, but if the soft tissue alone moved, the reflectors would not move. Alternatively, attaching reflectors to the scalp by adhesive, a head band or a reflective band would suffice, since the soft tissue moves only slightly relative to the cranial bones. Further, it is possible to place up to 16 reflectors around the body to determine unwanted movement. This will also allow determination of symmetric vs. asymmetric movements as well as possible harmonic movements.

At the same time, electrocardiogram (EKG) electrodes can be placed on the wrist and leg for bipolar recordings by an EKG unit 12. This will allow for correlation of the movements of the heartbeat with the motion detected by the intercostal reflector, which is needed for the eventual elimination of heartbeat movement from the cranial bone reflectors. Similarly, electrodes can be placed over the temporal, parietal, frontal and occipital bones for analysis by an EMG (electromyographic) unit 13. These are bipolar leads that will record electromyographic activity. This will allow us to eliminate activity due to voluntary or involuntary muscular activity around the scalp. The subject is then asked to relax for a period of 2 minutes. At that time, data is gathered for 30 to 60 seconds.

The system make use of a commercially-available instrument for detecting minute motions in two or three dimensions, this instrument being the MacReflex instrument marketed by Qualisis Corporation, which is designed for the study of minute movements in mechanisms such as automobiles. This instrument includes two infrared video cameras 14 to perform two and three-dimensional motion analyses. One video camera can be used to perform a two-dimensional motion analysis. Cameras 14 are coupled to a data aquisition unit 16 whose outlet is fed to a computer 17.

The instruments emit infrared light which reflects from specialized infrared reflectors to be received by the cameras. Images are acquired at 50 to 100 Hz. The video cameras and the image analyzer, associated therewith are capable of motion resolution of 1/30,000 of the visual field. Since the field of view of the skull is 30 cm, the system can resolve movement of at least 10 u.

In the simplest configuration, parietal bone movement alone can be analyzed using a 2D set-up as an example of movement of all of the cranial bones. In this form, one camera is aligned to face the subject from the superior aspect of the skull while the subject is in the supine position. A total of six reflector element can be place strategically on the subject.

Figure 2:
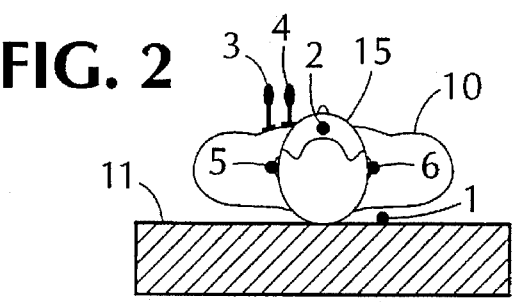
FIG. 2 illustrates the placement of the reflector elements on the patient.

These are schematically represented in FIGS. 1 and 2. Reflector element 1 is placed on the table surface 10 adjacent to the subject's head 15. Reflector element 2 is adhered to the area directly over the bregma, which faces the camera and is closest to it when the subject is in the supine position. The bregma is the junction of the sagittal and coronal sutures at the top of the skull. Reflector element 3, is mounted on the tip of a 10 cm tower (so that its view is not blocked by the head), the base of the tower being placed on the chest at the left fifth intercostal space (mid-clavicular). Reflector element 4 (also a 10 cm tower reflector) has its base placed two inches left of the xiphoid process. Reflector element 5 is attached to an acupuncture pin which in turn is inserted and anchored to the left parietal bone. Reflector element 6 is also attached to an acupuncture pin which in turn is inserted and anchored to the right parietal bone.

The parietal bone reflector element will allow determination of parietal bone movement. The reflectors on the intercostal space and the chest will allow quantification of movement caused by the heart beat and by respiratory movements. Since each reflector's movement can be analyzed relative to another one, the movement of the parietal bones can be analyzed relative to the stationary reflector, while eliminating (subtracting) overall head movement and movement from the heart or the chest.

A 16 channel EMG unit 13 can be used to record electrical activity (and subsequent muscle movement) from the scalp. Two bipolar electrodes are placed on the temporal, parietal, frontal and occipital bones. The data is fed to the EMG data acquisition unit, which then provides analog input to the computer's analog input board. The computer then stores the EMG information and reports it on the position-time scale in conjunction with the kinematic data.

Finally, the bipolar leads of the EKG unit 12 can be used to compare the movements obtained on the intercostal reflector. The bipolar leads are attached to the leg and limbs with high performance surface monitoring electrodes. The data is fed to the computer via its analog input board, which compiles kinematic data and is stored as a separate "mark" on the position-time scale. This will allow correlation of the intercostal reflector movement and the movement of the parietal bones.

The MacReflex software associated with a data acquisition unit 16 and computer 17 is intended to acquire data and analyze it according to the relative positions of the markers which the experimenter predetermines before each trial. Marker positions are calculated in absolute dimensions in a 2D or 3D matrix. Calculations are also made for markers relative to other ones. Analyses of position vs. time, acceleration and angle change between markers are performed automatically. Data is saved by subject number. Means and standard deviations for multiple tests and for multiple subjects can be compared using a Student's t Test.

Correlations can also be made between movement of the reference markers, and the EKG and EMG indications. These calculations are also performed automatically. In this way, movement attributable to other body motions and the actual movement of the cranial bones can be compared and analyzed.

Movement from the cranial bones cannot be masked or confused by other body movements. To understand why this is, one must understand the MacReflex kinematic system and its filtering, data acquisition and analytical specifications. This particular kinematic system employs the method of reference marking. This means that any marker movement is calculated relative to another marker in an X or Y coordinate, not both. For example, if the parietal bones are marked with reflectors, the subject can quite literally shake his/her head during measurement, or oscillate the reflectors in random directions while mounted on the needle (like "antenna sway"). However, the system will only measure the relative separation of the markers in the X or Y plane. Subtracting one from the other eliminates hyperbolic variants. Therefore, the movement detected is due purely to marker separation plotted over time. There is simply no other reason the markers (therefore the needles, and therefore the bones) would change their relative distances other than that which would be obtained by physical movement of their anchor points away or towards each other.

Just why the bones move is another problem. Could it be due to movement generated by respiration or the heart beat or some other physiological movement? This is the reason we try to identify and eliminate these variables with placing markers on the chest. Just as the system filters out unwanted head movement, it filters out movement from the chest. Indeed, we could place up to sixteen markers at strategic locations to try to detect a coordinated movement. We could even determine if such movements cause a harmonic motion which then moves the cranial bones. These and other issues need to be determined, and most are based on obtaining empirical data.

Cameras 14 are aligned to face the subject 10 from the superior aspect of the skull while the subject was in the supine position. The skin overlying the posteriolateral region of each parietal bone was sponged with alcohol, and a 1 inch #3 acupuncture needle (sterile and disposable) was inserted through the scalp and into each parietal bone on its posteriolateral aspect. Another needle was anchored to the midline of the frontal bone. Quarter inch diameter hemispherical infrared reflectors were then attached to the needle shafts. One reference reflector was also attached to the skin overlying bregma using denture paste (denture paste is tacky enough to stick to the skin while holding a reflector firmly in place, yet can be wiped off cleanly).

Anchoring the reflectors directly to the cranial bone with acupuncture needles is essential to detect movement of the bony structures alone. Thus, if the bone moves, the reflectors will move; if the soft tissue alone moves, the reflectors will not move. By firmly inserting the needle into the bone, it became well anchored. Movement of the reflectors (therefore, bone) could then be determined in an "X" and "Y" matrix. Reflectors are placed on the chest in order to subtract heart and respiratory movements.

At the beginning of the test, the subject was asked to relax for a period of 2 minutes. At that time, kinematic data was gathered for up to 30 seconds. In one trial, an osteopathic physician simultaneously and subjectively determined changes in cranial movement. This was performed by the subject laying her head in the physician's hands while the kinematic data was being acquired. His determinations of maximal and minimal parietal bone movement were timed and logged by an independent observer (since a foot switch for the physician has not yet been connected to the system). This allowed direct correlation of the motion analysis with the subjective evaluation. At no time during the test period did the physician see the results of the data acquisition.

Before being removed, the acupuncture needles were determined to still be anchored to the bone, assuring that they had not become dislodged during testing. If they had become dislodged, they were re-inserted and the test was re-started.

Reflector positions were calculated in absolute dimensions in a 3D matrix. Calculations were made for reflectors relative to each other. Analyses of position vs. time were performed automatically. Due to the small subject sample number (N=3), statistical evaluations were not performed. However, the empirical data could be qualitatively compared since the results were so dramatic.

As in the initial preliminary studies, it was possible to compare one reflector to another quite easily. Substracting unwanted movement from the head was performed automatically.

Three normal, healthy subjects, each had at least two tests performed. Two subjects were male (#1, age 24; #2, age 40) and one was female (#3, age 24).

The data obtained from each subject in two or more tests was consistent with respect to movement frequency in the same subject. However, the relative differences in movement frequency between subjects were slightly different. In all tests, the frequency was rhythmic and did not vary.

Subjects 1, 2 and 3 had frequencies of 11, 7 and 12 cycles/minute, respectively. When the physician subjectively determined frequency by placing his hands on the head, the frequency did not change, although the total excursion changed (see below).

Total excursion (maximal minus minimal reflector distances during a cycle of expansion and contraction of the bones) varied from subject to subject. Absolute total excursions ranged from approximately 20 u (in subject 2) to over 800 u (in subject 3). Additionally, when the physician placed his hands on the head of subject 3, the total excursion greatly reduced, while absolute skull diameter changed markedly.

Figure 3:
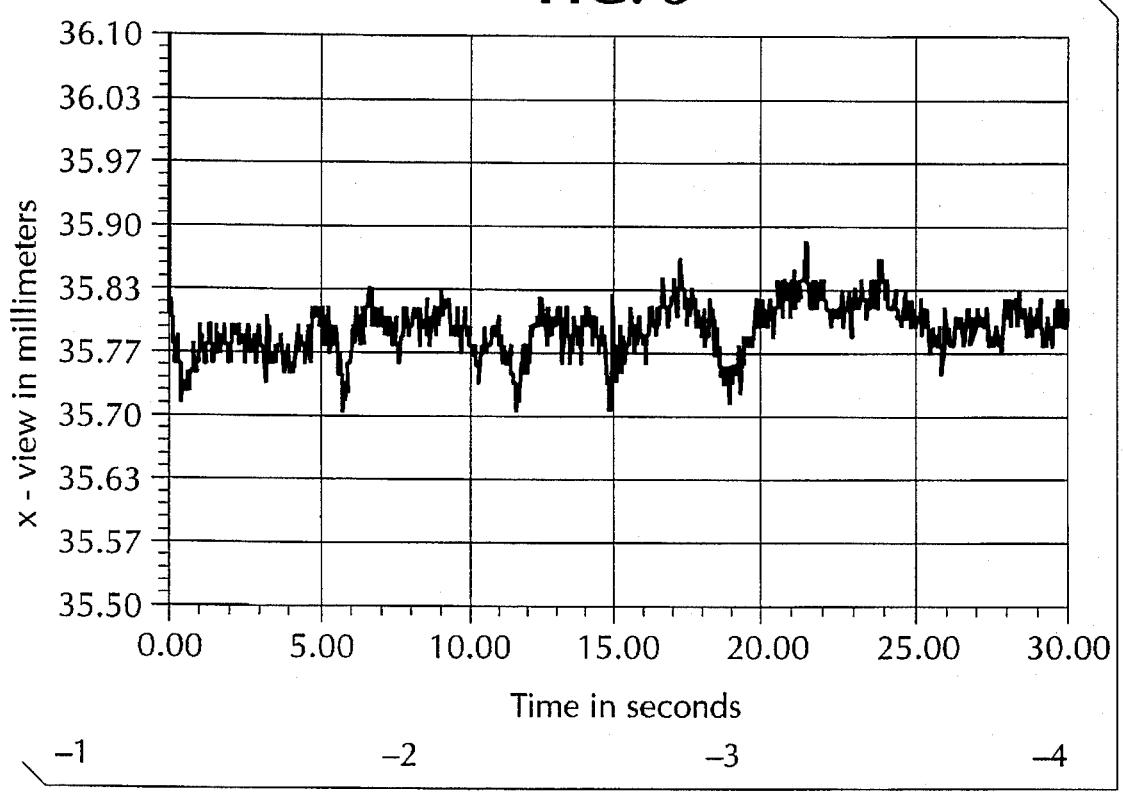
FIG. 3 is a three-dimensional analysis of a right parietal bone reflector element relative to a stationary bregma reflector element.

An example of the data obtained is shown in FIG. 3. This is a position-time measurement of parietal bone movement during one test in subject 1. Rhythmic movement with a total excursion of approximately 100 u was observed. A positive deviation denotes increasing separation of reflectors, and therefore, outward expansion of the bones. In osteopathic terms an outward movement is referred to as an "flexion," an inward movement being a "extension."

Figure 4:
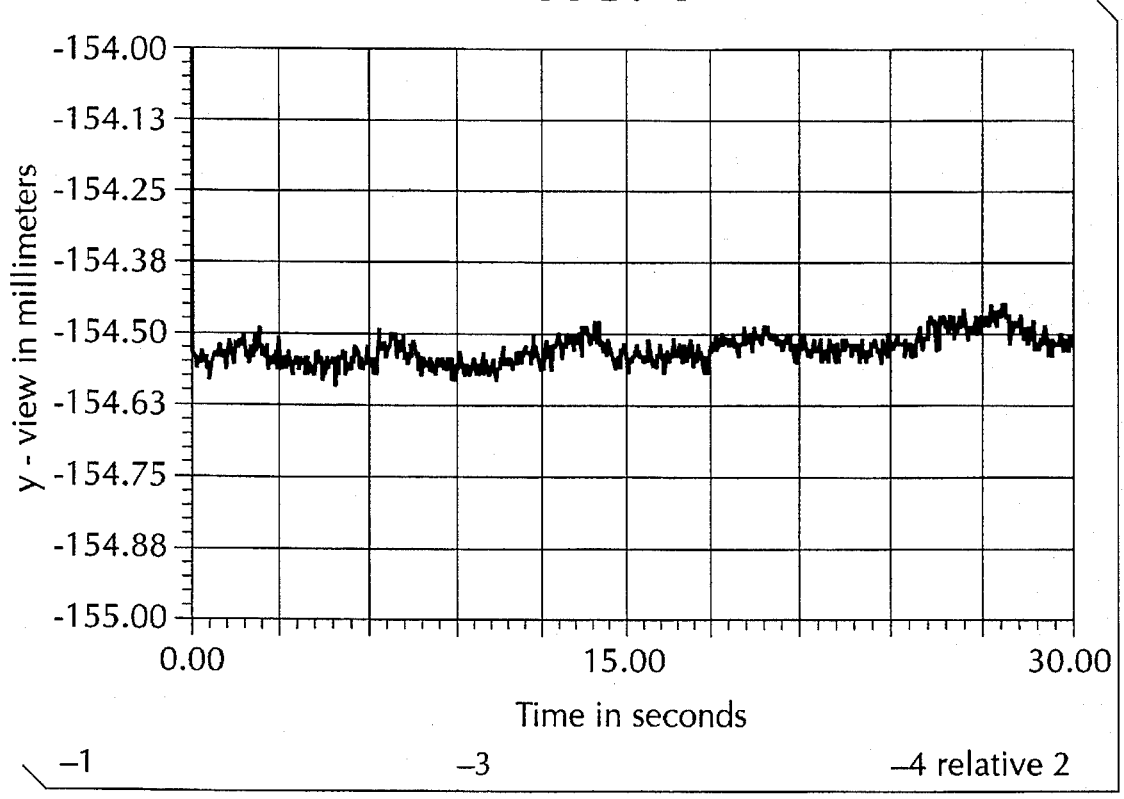
FIG. 4 is a three-dimensional analysis of a frontal bone reflector element relative to a stationary bregma reflector element.

FIG. 4 represents simultaneous measurement of the movement of the frontal bone in subject 1. This graph plots movement of the frontal bone reflector in the "Y" direction relative to the stable reflector at bregma. As in FIG. 3, a positive deviation denotes increasing separation of reflectors, and therefore, an outward movement or expansion of the frontal bone (since bregma is stationary). Note how this frequency is identical to the frequency of the parietal bone reflectors in FIG. 3. Most importantly, note how the oscillations were rhythmic and approximately 180° out of phase with the parietal bone reflectors. This denotes maximal outward movement of the frontal bone during maximal inward movement of the parietal bones. Thus a cycle of extension and flexion can be observed, using this system.

Figure 5:
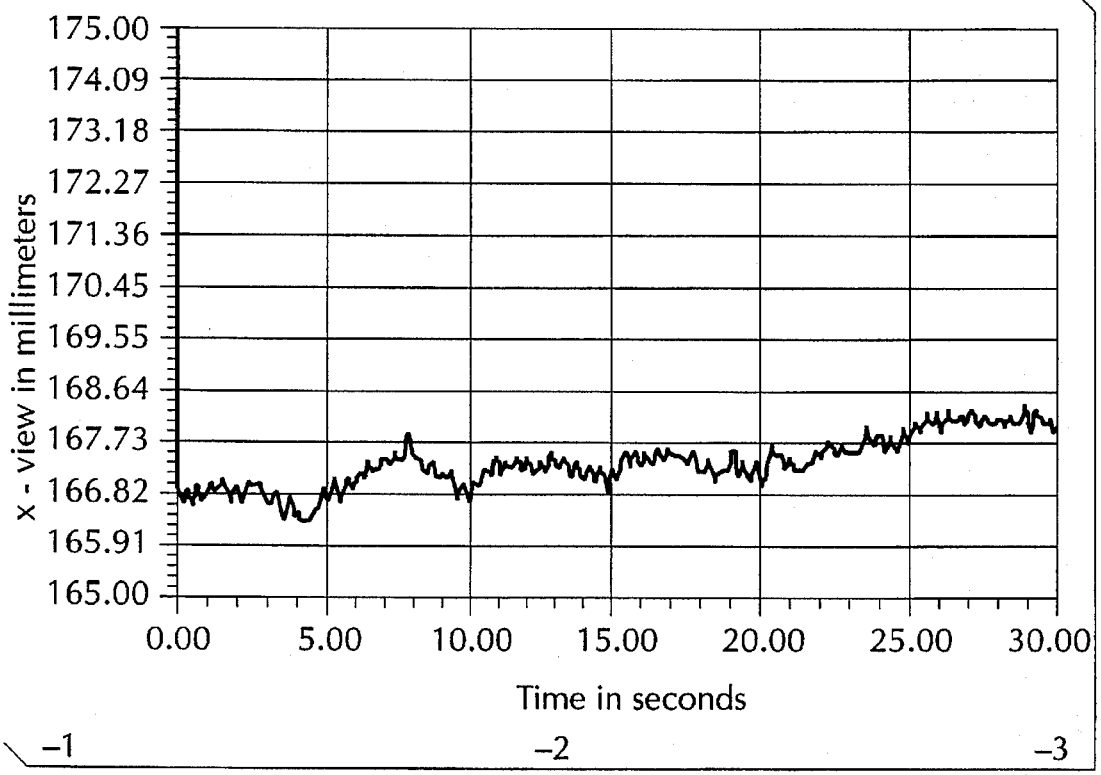
FIG. 5 is a three-dimensional analysis of a right parietal bone reflector element relative to a left parietal bone reflector element.
Figure 6:
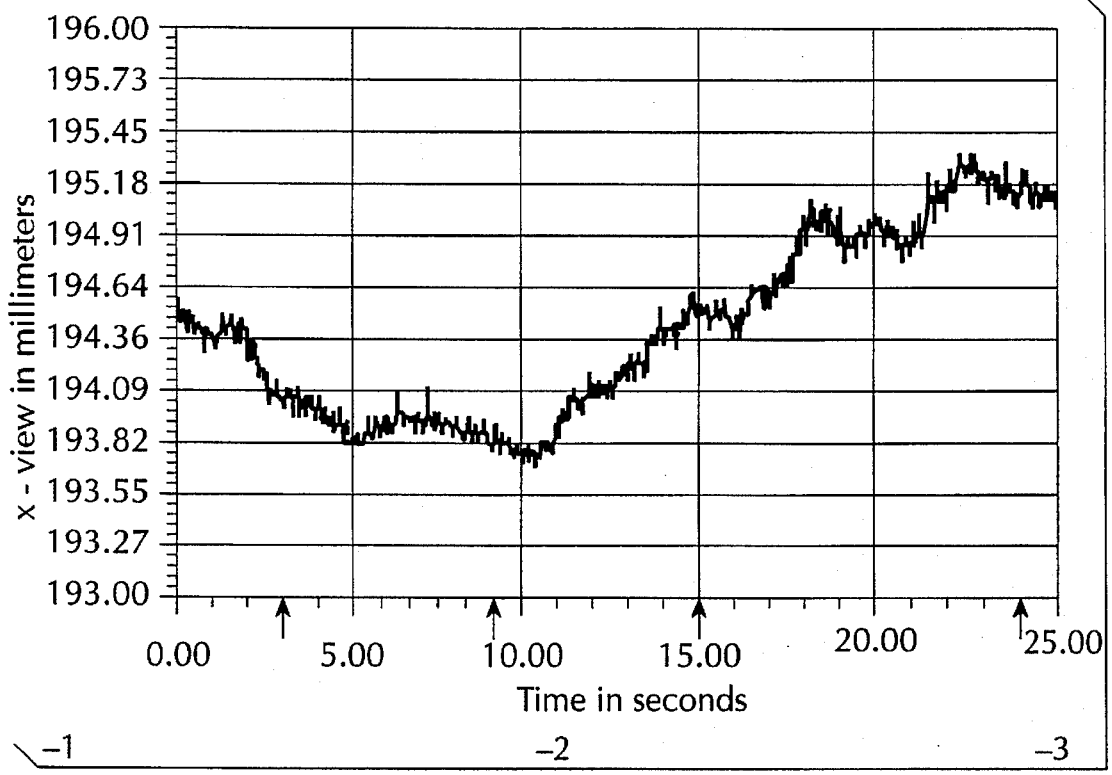
FIG. 6 is a three-dimensional analysis of a right parietal bone reflector element relative to a left parietal bone reflector element.

Data obtained from subject 3 is shown in FIG. 5, and represents movement of the parietal bones. As in the other subjects, note the rhythmic movement (increasing positive is increasing bone separation or extension). Note the total excursion of approximately 800μ, at a frequency of approximately 12 cycles/minute. FIG. 6 represents data obtained in another test in this subject, where a trained physician observer now placed his hands on the head. Time stamps (small arrows) were overlayed on the kinematic data which represent the subjective evaluations of maximal separation (extension) of the parietal bones as determined by the observer. As can be readily seen, the subjective evaluation corresponded well with the objective kinematic data with respect to frequency and movement. The subjective evaluations consistently preceded the actual movement, where a minimum of parietal bone separation (flexion) was noted.

Interestingly, and as noted above, in subject 3 the maximal excursion greatly reduced with observer involvement from 800μ to below 600μ. However, the absolute distance between reflectors decreased, recovered and then increased (FIG. 6). This suggests that the absolute diameter of the skull decreased then increased. The changed lateral distance was 2.2 mm over a 10 second period.

The following is a more detailed explanation of FIGS. 3 to 6.

FIG. 3 is a position-time analysis of right parietal bone reflector relative to left parietal bone reflector in subject 1. Oscillations represent relative movement (excursion) between reflectors. A positive deviation denotes maximal separation, while a negative deviation represents minimal separation. Total excursion was approximately 100μ (i.e., note amplitude of "hump" between 15 and 20 seconds of 35.70 mm to 35.80 mm). Frequency was 11 cycles/minute (calculated by counting the 5.5 "humps" in the 30 second graph interval).

FIG. 4 is a position-time analysis of the frontal bone reflector relative to the stationary bregma reflector in subject 1. Thus, oscillations represent movement (excursion) of the frontal bone. A positive deviation denotes maximal separation, while a negative deviation represents minimal separation. Total excursion was approximately 100 u (i.e., note amplitude of "dip" at 15 seconds from −154.61 mm to −154.51 mm). Frequency was 11 cycles/minute (calculated by counting the 5.5 "dips" in the 30 second graph interval).

FIG. 5 is a position-time analysis of right parietal bone reflector relative to left parietal bone reflector in subject 3. Oscillations represent relative movement (excursion) between reflectors. A positive deviation denotes maximal separation, while a negative deviation represents minimal separation. Total excursion was approximately 800μ (i.e., note amplitude of "hump" between 10 and 15 seconds of 166.82 mm to 167.65 mm). Frequency was 12 cycles/minute (calculated by counting the 6 "humps" in the 30 second graph interval).

FIG. 6 is a position-time analysis of right parietal bone reflector relative to left parietal bone reflector in subject 3. In this test of the same subject as in FIG. 3, the physician observer placed his hands on the subject's head to subjectively determine frequency. Subjective determinations of maximal change were time stamped as "arrows". Oscillations represent relative movement (excursion) between reflectors. A positive deviation denotes maximal separation, while a negative deviation represents minimal separation. Total excursion ranged from approximately 200μ to 600μ (i.e., for 200μ, note amplitude of "hump" between 5 and 10 seconds of 193.70 mm to 193.90 mm). Frequency was 12 cycles/minute (calculated by counting 4 "humps" in a 20 second interval). Note the marked minimum and maximum reflector separations (at 10 seconds 23 seconds, respectively), denoting changes in absolute skull diameter.

Conclusion

For the first time in man, verification and quantification of cranial bone mobility has been achieved. The system is capable of detecting small movements, which could efficiently filter out extraneous motion around the skull, thereby allowing the direct detection and measurement of cranial bone movements. This lays the foundation for the exploration of the physiological significance of cranial bone mobility.

And the system facilitates the practice of cranial osteopathy, for one can determine the effect of cranial manipulation and so manipulate cranial bones as to bring about a recovery of a normal rhythmic pattern which had been disturbed by a pathological condition. The system is also useful for diagnostic and screening purposes to quantify cranial mobility.

While there has been disclosed a preferred embodiment of a diagnostic system in accordance with the invention, it is to be understood that many modifications may be made therein without departing from the essential features of the invention.

I claim:

1. A diagnostic system for detecting and indicating cranial movements in a human subject whose brain case is composed of a plurality of articulated bones which define the cranium, which bones normally undergo oscillatory motion, said system comprising:

(a) reflector elements placeable on selected bones of the cranium whereby the elements are caused to vibrate as a function of the oscillatory motion of these bones;

(b) an infrared camera directed at the cranium which during a test period emits infrared light that is reflected by the elements and is picked up by the camera to produce in an image analyzer information regarding relative motion between the vibrating elements; and (c) a computer to which said information is supplied, said computer being programmed to reconstruct the relative motion as a diagram illustrating cranial movement during the test period.

2. A system as set forth in claim 1 in which each reflector element is formed by a reflector mounted on an acupuncture pin insertable in the bone.

3. A system as set forth in claim 1 including means to eliminate from the system the effects of motion from other active parts of the body of the subject.

4. A system as set forth in claim 3 in which said means includes an EMG unit associated with reflector elements placeable on the torso of the subject.

5. A system as set forth in claim 3, wherein said means includes an EKG unit associated with electrodes attachable to the limbs of the subject.

6. A diagnostic technique for indicating oscillatory motion of a plurality of articulated bones that define the cranium of a human subject to determine the subject's condition, said technique comprising the steps of:

(a) placing on selected bones of the cranium reflector elements which then vibrate as a function of the oscillatory motion of these bones;

(b) directing at the cranium light rays which are reflected by the elements during a test period and are picked up by a camera to produce an image providing information regarding relative motion between the elements; and (c) supplying the information to a computer programmed to reconstruct said relative motion as a diagrammatic reading illustrating cranial movement during the test period.

7. A technique as set forth in claim 6 in which the light is infrared light rays.

8. A technique as set forth in claim 6 further including the steps of placing electrodes on the head and torso of the subject which are coupled to an EMG unit to indicate muscle activity, the EMG indication being subtracted from the reading so as to eliminate the effect of muscle movement on the reading of cranial movement.

9. A technique as set forth in claim 6 further including the steps of placing electrodes on the torso which are coupled to an EKG unit to provide EKG indications which are subtracted from the reading to eliminate the effect of the heart beat on the reading of cranial movement.

* * * * *